US007976837B2

(12) United States Patent
Abe et al.

(10) Patent No.: US 7,976,837 B2
(45) Date of Patent: Jul. 12, 2011

(54) METHOD OF PREVENTING AND TREATING BRAIN INFARCTION

(75) Inventors: Koji Abe, Okayama (JP); Junichi Kawagoe, Saitama (JP)

(73) Assignee: Kowa Company, Ltd., Nagoya-shi (JP)

(*) Notice: Subject to any disclaimer, the term of this patent is extended or adjusted under 35 U.S.C. 154(b) by 1043 days.

(21) Appl. No.: 11/573,429

(22) PCT Filed: Jun. 17, 2005

(86) PCT No.: PCT/JP2005/011122
§ 371 (c)(1),
(2), (4) Date: Feb. 8, 2007

(87) PCT Pub. No.: WO2006/016450
PCT Pub. Date: Feb. 16, 2006

(65) Prior Publication Data
US 2009/0263374 A1 Oct. 22, 2009

Related U.S. Application Data

(60) Provisional application No. 60/600,375, filed on Aug. 11, 2004.

(51) Int. Cl.
*A61K 38/48* (2006.01)
(52) U.S. Cl. .................................................. 424/94.64
(58) Field of Classification Search ................ 424/94.64
See application file for complete search history.

(56) References Cited

U.S. PATENT DOCUMENTS
6,124,291 A * 9/2000 Berryman et al. ............ 514/249

FOREIGN PATENT DOCUMENTS
| WO | 99/50254 A1 | 10/1999 |
|---|---|---|
| WO | 2004/080373 A2 | 9/2004 |

OTHER PUBLICATIONS

Supplementary European Search Report dated Jul. 17, 2009 issued in corresponding European Application No. 05751580.1.
Mayer, S. A., "Intracerebral Hemorrhage: Natural History and Rationale of Ultra-Early Hemostatic Therapy", Intensive Care Medicine, Oct. 2002, pp. S235-S240, vol. 28.
Wang, J. et al., "Up-regulation and Activation of Proteinase-Activated Receptor 2 in Early and Delayed Radiation Injury in the Rat Intestine: Influence of Biological Activators Proteinase-Activated Receptor 2", Radiation Research, Nov. 1, 2003, pp. 524-535, vol. 160, No. 5.
Al-Ani, B., et al., "Proteinase-Activated Receptor-2: Key Role of Amino-Terminal Dipeptide Residues of the Tethered Ligand for Receptor Activation", Molecular Pharmacology, Jan. 2004, pp. 149-156, vol. 65, No. 1.
Milia, A. F., "Protease-Activated Receptor-2 Stimulates Angiogenesis and Accelerates Hemodynamic Recovery in a Mouse Model of Hindlimb Ischemia", Circulation Research, Aug. 23, 2002, pp. 346-352, vol. 91, No. 4.

Valeria S. Ossovskaya et al., "Protease-Activated Receptors: Contribution to Physiology and Disease", Physiological Reviews, vol. 84, pp. 579-621, 2004, The American Physiological Society, Maryland, USA.
Scott R. Macfarlane et al., "Proteinase-Activated Receptors", Pharmacology Reviews 53, pp. 245-282, 2001, The American Society for Pharmacology and Experimental Therapeutics, USA.
Sverker Nystedt et al., "Molecular cloning of a potential proteinase activated receptor", Proc. Natl. Acad. Sci. USA, vol. 91, pp. 9208-9212, 1994, Cornell University Medical College, NY, USA.
Virginia L. Smith-Swintosky et al., "Protease-Activated Receptor-2 (PAR-2) Is present in the Rat Hippocampus and Is Associated with Neurodegeneration", Journal of Neurochemistry, vol. 69, pp. 1890-1896, 1997, Lippincott-Raven Publishers, Philadelphia, USA.
Frank Striggow et al., "Four different types of protease-activated receptors are widely expressed in the brain and are up-regulated in hippocampus by severe ischemia", European Journal of Neuroscience, vol. 14, pp. 595-608, 2001, Federation of European Neuroscience Societies.
E. Sander Connolly et al., "Procedural and Strain-related Variables Significantly Affect Outcome in a Murine Model of Focal Cerebral Ischemia", Neurosurgery, vol. 38, pp. 523-532, 1996, Columbia University, College of Physicians and Surgeons, NY, USA.
Marina Molino et al., "Endothelial Cell Thrombin Receptors and PAR-2", The Journal of Biological Chemistry, vol. 272, pp. 11133-11141, Apr. 25, 1997, The American Society for Biochemistry and Molecular Biology, Inc., USA.
Wuyi Kong et al., "Luminal trypsin may regulate enterocytes through proteinase-activated receptor 2", Proc. Natl. Acad. Sci. USA, vol. 94, pp. 8884-8889, 1997, The National Academy of Sciences, USA.
Bahjat Al-Ani et al., "Detection of functional receptors for the proteinase-activated-receptor-2-activating polypeptide, SLIGRL-$NH_2$, in rat vascular and gastric smooth muscle", Canadian Journal of Physiology and Pharmacology., vol. 73, pp. 1203-1207, 1995, Canada.
Atsufumi Kawabata et al., "Activation of Protease-Activated Receptor-2 (PAR-2) Triggers Mucin Secretion in the Rat Sublingual Gland", Biochemical and Biophysical Research Communications, vol. 270, pp. 298-302, 2000, Academic Press, Japan.

(Continued)

*Primary Examiner* — Ruth Davis
(74) *Attorney, Agent, or Firm* — Westerman, Hattori, Daniels & Adrian, LLP

(57) ABSTRACT

The present invention is intended to clarify the relationship between PAR-2 and cerebral infarction and thereby provide an efficient method of preventing and treating cerebral infarction, as well as a pharmaceutical composition therefore. Namely, the present invention relates to a method of preventing and treating cerebral infarction by activating PAR-2 and/or promoting expression of PAR-2 gene. The present invention further relates to a pharmaceutical composition for preventing and treating cerebral infarction, comprising one, or two or more of the active ingredients selected from the group consisting of a PAR-2 activator and/or a PAR-2 gene expression promoter; as well as a pharmaceutically acceptable carrier. It further relates to a method of screening an active ingredient for preventing and treating cerebral infarction using as an indicator the PAR-2 activation promoted by a test substance.

3 Claims, 2 Drawing Sheets

OTHER PUBLICATIONS

Sobey, C. G. et al.; "Evidence for Selective Effects of Chronic Hypertension on Cerebral Artery Vasodilatation to Protease-Activated Receptor-2 Activation"; Stroke; A Journal of Cerebral Circulation Sep. 1999 LNKD-PUBMED: 10471447, vol. 30, No. 9, Sep. 1999, pp. 1933-1940: di, ISSN: 0039-2499.

European Communication pursuant to Article 94(3) EPC dated Jun. 25, 2010, issued in European Patent Application No. 05751580.1.

Guang Jin et al.; "Deficiency of PAR-2 gene increases acute focal ischemic brain injury"; Journal of Cerebral Blood Flow & Metabolism, vol. 25, pp. 302-313, 2005. Cited in the int'l. search report.

G. S. Cottrell et al.; "Protease-activated receptor 2: activation, signalling and function"; Biochemical Society Transactions, vol. 31, part 6, pp. 1191-1197. Cited in the int'l. search report.

M. Steinhoff et al.; "Agonists of proteinase-activated receptor 2 induce inflammation by a neurogenic mechanism"; Nature Medicine, vol. 6, No. 2, pp. 151-158, Feb. 2000. Cited in the int'l. search report.

S. R. MacFarlane et al.; "Proteinase-Activated Receptors"; Pharmacological Reviews, vol. 53, No. 2, pp. 245-282, 2001. Cited in the int'l. search report.

Ahamad Hassan et al.; "Markers of endothelial dysfunction in lacunar infarction and ischaemic leukoaraiosis", Brain, vol. 126, pp. 424-432, 2003. Cited in the int'l. search report.

International Search Report of PCT/JP2005/011122, date of mailing Aug. 30, 2005.

International Preliminary Report on Patentability dated Feb. 22, 2007, issued in corresponding PCT/JP2005/011122, with Form PCT/IB/338.

* cited by examiner

A
WT

B
KO

C

Ischemic infarction in KO mouse after 24h of tMCAO

C

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 1

Ser Leu Ile Gly Lys Val
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 2

Ser Leu Ile Gly Arg Leu
1               5

METHOD OF PREVENTING AND TREATING BRAIN INFARCTION

TECHNICAL FIELD

The present invention relates to prevention and treatment for cerebral infarction by activating PAR-2 and/or promoting the expression of PAR-2 gene. Particularly, the invention relates to the method of preventing and treating cerebral infarction using a PAR-2 activator and/or a PAR-2 gene expression promoter. The present invention further relates to a pharmaceutical composition for preventing and treating cerebral infarction, comprising one, or two or more active ingredient(s) selected from the group consisting of a PAR-2 activator and/or PAR-2 gene expression promoter; as well as a pharmaceutically acceptable carrier. The invention further relates to a method of screening an active ingredient for preventing and treating cerebral infarction using as an indicator the PAR-2 activation promoted by a test substance.

BACKGROUND ART

Brain requires large quantity of energy to maintain its internal environment and its activity so that the brain needs a constant supply of glucose and oxygen for its normal metabolism. The impaired cerebral energy metabolism due to the decreased blood flow inhibits brain activity, whereby inhibits the function of a corresponding organ controlled by the damaged area of the brain. Such an abnormality in physical condition or bodily function associated with partial and sudden brain disorder is essential to cerebrovascular disorder (cerebral stroke). Cerebrovascular disorder is classified as "cerebral infarction" wherein ischemic necrosis is caused in the perfused area in the brain tissue by blockage of blood flow due to the occlusion of the artery of the brain; "cerebral hemorrhage" caused by the rupture of a blood vessel in the brain, and "transient cerebral ischemic attack" wherein observed the temporal diminution of brain blood flow with rapid restoration thereof. Moreover, "cerebral infarction" can generally be classified into two major categories such as cerebral thrombosis and cerebral embolism by its causations.

Cerebrovascular disease was the first leading cause of death until replaced by cancer in 1981 since tuberculosis had been brought under control; and now is the third leading cause of death which in turn was replaced by cardiac disease in 1985. Cerebrovascular disease was the third leading cause of death in Japan in the (fiscal) year of 1999 with the rate of 110.8 deaths/100,000 population (the Ministry of Health, Labor and Welfare statistics in the year of 1999.) And, the rate of death from cerebral infarction was reported as 57.7 per 100,000 population. However, it is noted that the patients suffering from cerebral infarction including chronic phase has significantly been increased in number compared to those who are suffering from cancer and cardiac disease associating with the increased longevity. Although majority of nonfatal cerebral infarctions have relatively small lesions, they have come to attract people's attention in consequence of the aging of population as high incidence of cerebellar infarctions results in multiple infarct dementias (cerebrovascular dementia). Therefore, not only the development of the treatment but also the establishment of prophylactic strategy and the manufacture of prophylactics against the cerebrovascular diseases are desired. Nevertheless, potent prophylactics have not been developed yet.

Starting with X-ray computed tomography developed in 1970s, the development of various medical imaging technologies for diagnosis enabled the early detection of the cerebrovascular diseases and contributed to the progress in revealing the pathophysiology thereof. Cerebroprotective agents, anti-platelet agents, antithrombin agents, etc. have been employed in the treatment of cerebral infarction, however, the therapeutic effects thereof are not sufficient enough, thus the more effective treatment is desired.

PAR-2 is a member of protease-activated receptors family, and PAR-1, PAR-2, PAR-3 and PAR-4 in PAR family have currently been cloned. PAR families are G protein-coupled receptors with seven-transmembrane domains, but its activation mechanism is significantly different from that of other seven transmembrane G proteins-coupled receptors. Particularly, proteases cleave at specific sites of amino-terminus within PAR molecule i.e. a receptor; a newly exposed terminus serves as tethered ligand, folding back onto the receptor, and thereby activating it (Physiol. Rev., 2003; 84:579-621; Pharmacol. Rev., 2001; 53:245-282). While PAR-1, PAR-3 and PAR-4 are activated by thrombin, PAR-2 is not activated by thrombin but activated by trypsin or tryptase.

PAR-2 was cloned by Nystedt et al. in 1994 (Proc. Natl. Acad. Sci. USA, 1994; 91:9208-9212). Unlike the other PAR families, PAR-2, as mentioned above, is activated by the different proteases such as trypsin or tryptase. Other PAR-2 activators are synthetic peptides having the same amino acid sequences as aforementioned tethered ligand, the derivatives thereof trans-cinnamoyl-LIGRL-NH2, trypsins, tryptases, tissue factors/factor VIIa, factor Xa, acrosin which is a sperm proteases, tryptic serine proteases identified from the brain of a rat (Physiol. Rev., 2003; 84,579-612; Pharmacol. Rev., 2001; 53,245-282).

PAR families are widely expressed in many organs and tissues in vivo, and involvement of PAR activations in physiological significances and pathological conditions has been investigated in various cells, tissues, and animal models. Exertion of versatile physiological functions of PARs in vivo has been revealed as 1) control of blood coagulation and activation of vascular endothelial cells, 2) control of contraction and relaxation of the gastrointestinal tract, as well as secretion of saliva or digestive juice, 3) control of contraction and relaxation of respiratory tract, as well as secretion of cytokines or proteases from the bronchial epithelial cells, 4) control of inflammation reaction, and 5) control of survival of the central neuronal cells, edema and nociception (Physiol. Rev., 2003; 84:579-621; Pharmacol. Rev., 2001; 53:245-282).

In addition to the above-mentioned functions, it is reported in the in vitro and in vivo experimental systems that PAR-2 causes leukocyte rolling and adhesion; neutrophil infiltration; secretion of inflammatory cytokines and leakage of plasma proteins; as well as onset and exacerbation of arterial sclerosis, skin inflammation, arthritis and acute inflammation (Physiol. Rev., 2003; 84:579-621; Parmacol. Rev., 2001; 53:245-282).

PAR-2s, expressed in various cells in the brain, are believed to be one of the factors that exacerbates pathological conditions associate with nerve cell apoptosis in the brain because the experimental systems with cultured nerve cell demonstrated the dose-dependent cell death induced by addition of PAR-2 activating peptides to the cell culture (J. Neurochem., 1997; 69:1890-1896); and the correlation between nerve cell death under hypoxic condition and increased expression of PAR-2 (Eur. J. Neurosci., 2001; 14:595-608). However, the relationship between PAR-2 and cerebral infarction is still unrevealed.

DISCLOSURE OF THE INVENTION

Problems to be Solved by the Invention

An object of the present invention is to elucidate relationship between PAR-2s and cerebral infarction, and thereby provide methods of preventing and treating cerebral infarction as well as medicaments used therefore.

Means of Solving the Problems

The present inventors have conducted the study on application of PAR-2 inhibition to prevention and treatment of cerebral infraction in PAR-2 gene-deficient mouse, and surprisingly found that PAR-2 deficiency promoted the expansion of cerebral infraction site, and thereby completed the invention for the method of preventing and treating the cerebral infarction by activation of PAR-2 and/or promotion of PAR-2 gene expression.

Accordingly, the invention provides the method of preventing and treating cerebral infarction by activation of PAR-2 and/or promotion of PAR-2 gene expression. More specifically, the invention provides the method of preventing and treating cerebral infarction by administrating the effective amount of one or more active ingredients selected from the group consisting of a PAR-2 activator and/or a PAR-2 gene expression promoter to patients suffering form cerebral infraction or at risk of having it.

The invention further provides a pharmaceutical composition for preventing and treating cerebral infarction comprising one or more active ingredients selected from the group consisting of a PAR-2 activator and/or a PAR-2 gene expression promoter as well as a pharmaceutically acceptable carrier.

The invention further provides use of a PAR-2 activator and/or a PAR-2 gene expression promoter for manufacture of the preparation for preventing and treating cerebral infarction.

The invention further provides a method of screening an active ingredient for preventing and treating cerebral infarction using as an indicator the PAR-2 activation promoted by a test substance. For more detail, the invention provides a method of screening an active ingredient for preventing and treating cerebral infarction, comprising the screening of the test substance with the function of activating PAR-2 or promoting expression of PAR-2 gene by contacting the test substances with a cell expressing PAR-2 to determine expression or activity of PAR-2.

Effect of the Invention

The invention demonstrated that activation of PAR-2 or promotion of PAR-2 gene expression could be effective in preventing and treating the cerebral infarction by revealing the function of PAR-2 in the brain and clarifying the correlation of PAR-2 with cerebral infarction. Also, the invention demonstrated that one or more ingredients selected from the group consisting of a PAR-2 activator or a PAR-2 gene expression promoter could be the effective agents for preventing and treating the cerebral infarctions. The invention, thus, provides not only the effective method but also the effective agents for preventing and treating the cerebral infarctions.

BEST MODE FOR CARRYING OUT THE INVENTION

The present inventors examined the correlation of PAR-2 with cerebral infarction using male PAR-2-deficient mice (homozygous deficient mice: PAR-2$^{-/-}$ mice) generated by backcrossing with C57BL/6 mice for eight generations.

Initially, infarction volume in an infarction model was evaluated. More specifically, tMCAO model was prepared according to the methods of Connolly et al. (Neurosurgery, 1996; 38:523-531), wherein middle cerebral arteries (MCA) of a male PAR-2$^{-/-}$ mouse (KO) and a wild type mouse (WT) were blocked with a nylon suture under anesthesia, and after 60 minutes of the occlusion, blood flow was restored by withdrawal of the nylon suture. The brains were removed following decapitation at 24 hours after reperfusion, and 14 serial 10 µm-thick slices of longitudinal sections from each brain were cut at 600 µm intervals beginning at 1 mm from the front using a cryostat. Each slice was stained with cresyl violet, and the infraction area was measured with the use of computer-assisted image analysis software SigmaScan pro 5 (SPSS Inc.). Total infarct volume was calculated with the area of infarction and the distance between each slice; and values are expressed as mean±S.D.

Figure 1:
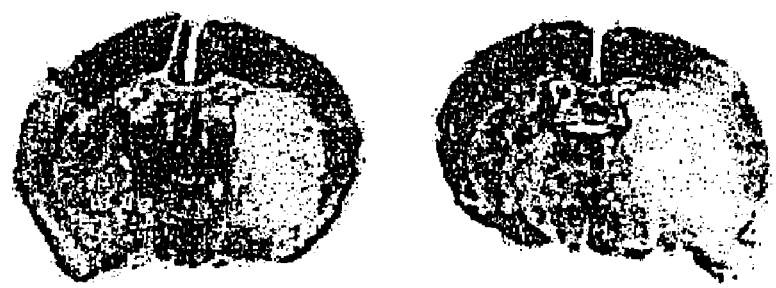
FIG. 1 shows the infarction area (A, B) and the infarction volume (C) at 24 hours after 60 minutes of transient middle cerebral artery occlusion (tMCAO) subjected to wild-type mice and PAR-2$^{-/-}$ mice (KO). As noted, the infarction area and infarction volume are significantly increased in KO compared with WT histopathologically (A, B) as well as statistically (C: n=6, P<0.05).
Figure 1:
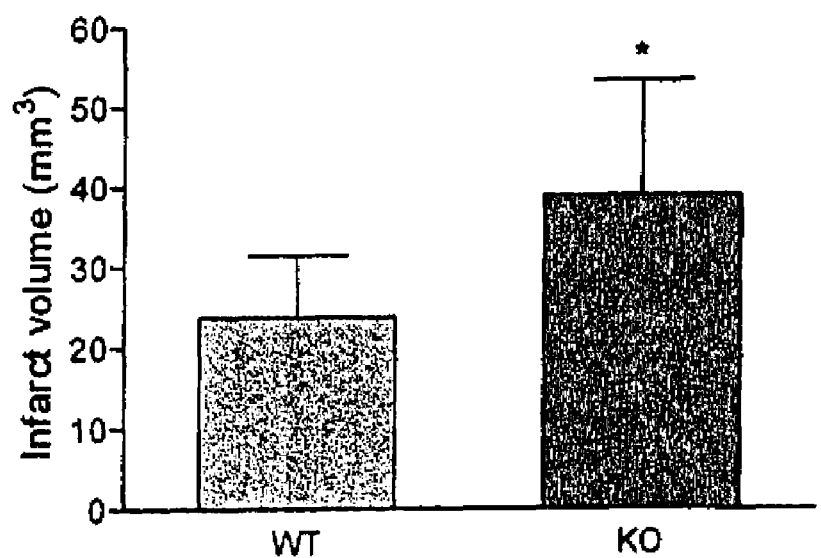

Results of representative cresyl violet stained image and infarction volume are shown in FIGS. 1A, 1B and 1C. Infarction area unstained by cresyl violet was significantly increased in KO (FIG. 1B) compared with WT (FIG. 1A), and infarction volume (FIG. 1C) was also significantly increased (p<0.05, Student's t-test) in KO (38.9±14.4 mm$^3$ (n=6)) compared with WT (23.8±7.7 mm$^3$ (n=6)). Thus, PAR-2 deficiency was revealed to be responsible for progression of cerebral infarction.

Secondly, apoptosis assay was performed. The brains at 24 hours after tMCAO were examined to detect DNA fragmentation using terminal deoxynucleotidyl dUTP nick-end labeling (TUNEL) kit (Trevigen, Gaithers-burg, Md., USA). More specifically, the brains, at 24 hours after reperfusion, were removed following decapitation and quickly frozen in liquid nitrogen and cut on a cryostat to 10 µm thickness of longitudinal sections to include striatum. The frozen sections fixed by 4% paraformaldehyde were incubated with digoxigenin-labeled dUTP in the presence of terminal deoxynucleotidyl transferase (TdT) at 37° C. for 1 hour, followed by incubated with horseradish peroxidase-conjugated anti-digoxigenin antibody for 1 hour at room temperature. Then the sections were stained with diaminobenzidine, and the number of TUNEL positive cell stainings were counted in the three 1×1 mm$^2$ regions of the inner boundary zone of subsequent infarction to calculate mean±S.D.

Figure 2:
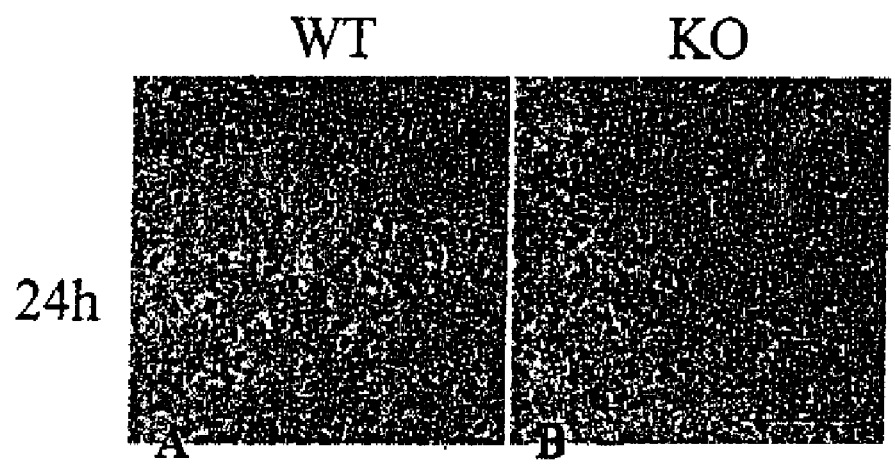
FIG. 2 shows TUNEL labeling (A, B) and the number of TUNEL positive cells (C) in the border of infarction area at 24 hours after 60 minutes of tMCAO subjected to wild-type mice and PAR-2$^{-/-}$ mice (KO).
Figure 2:
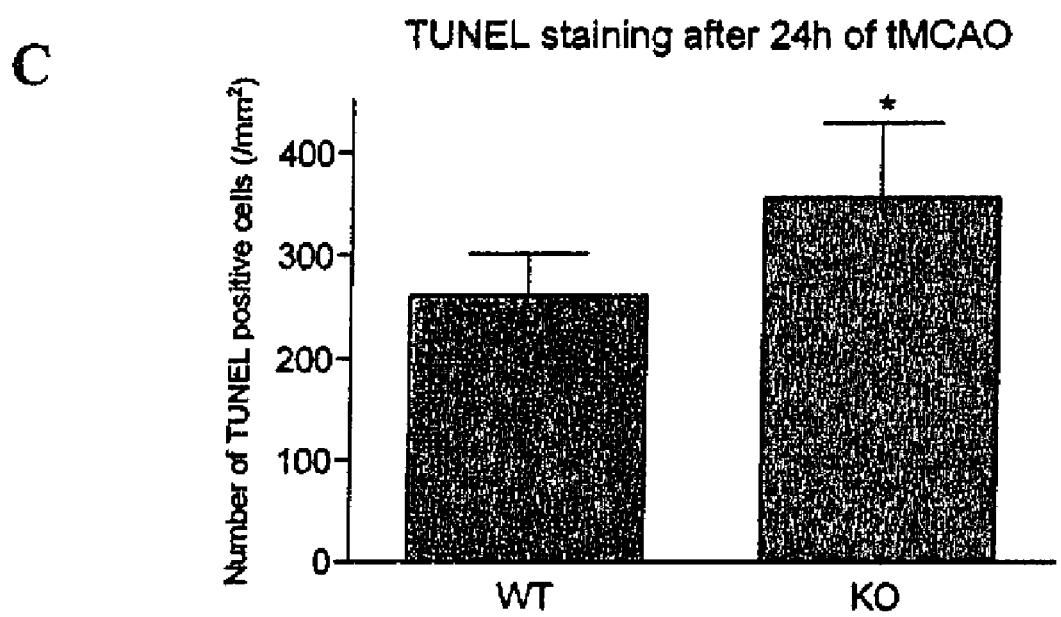

The results were shown in FIGS. 2A, 2B and 2C. TUNEL positive cells are mainly distributed around the border in the area where the blood is supplied through MCA of WT and KO, and TUNEL staining is recognized basically in the cell nucleus (FIG. 2A (WT), FIG. 2B (KO)). Further, the number of positive cells in KO (356.7±71.8, n=6) was significantly increased (p<0.05, student's t-test) compared with WT (261.2±41.3, n=6) (FIG. 2C). Thus, PAR-2 deficiency was revealed to be responsible for increase of apoptosis. Consequently, these results demonstrated that PAR-2 deficiency plays important role in progression of cerebral infarction.

The terms "activation of PAR-2" and/or "promotion of PAR-2 gene expression" used herein are intended to include any of the events resulting in the enhancement of PAR-2 functions.

The examples of a PAR-2 activator and/or a PAR-2 gene expression promoter of the present invention include PAR-2 stimulator which stimulates PAR-2 and thereby activates the function of PAR-2, as well as PAR-2 gene expression enhancer which enhances the expression of PAR-2 gene and thereby activates the function of PAR-2.

The Specific examples of a PAR-2 activators include PAR-2 ligands, PAR-2 ligand derivatives, trypsin, tryptase, tissue factors/VIIa factor, Xa factor, acrosin, trypsin-like serine protease, and the like. More specifically, the examples of peptides comprising the amino acid residues which activate receptors at cleavage site of PAR-2, include peptides having at least the sequence of LIG (one-letter notation for amino acid sequences), preferably peptides comprising 3 to 8 amino acids having the sequence sfLIG (one-letter notation for amino acid sequences), more preferably peptides having the sequences of SLIGKV (one-letter notation for amino acid sequences), i.e., SEQ ID NO. 1, or SLIGRL (one-letter notation for amino acid sequences), i.e., SEQ ID NO. 2, or the derivatives thereof.

A pharmaceutical composition of the present invention for preventing and treating the cerebral infarction comprising the above described a PAR-2 activator and/or a PAR-2 gene expression promoter as active ingredient(s); and pharmaceutically acceptable carriers, can be presented as the compositions suitable for oral or parenteral administration such as oral agents, injection solutions, suppositories, ointments and adhesive preparations using the conventional method known to those skilled in the art.

The solid oral formulation of the subject compositions may conventionally be presented as a tablet a coated tablet, granules, powder or a capsule by adding an excipient, and optionally adding a binder, a disintegrator, a lubricant, a coloring agent, and flavoring agents, etc. to the previously described PAR-2 activators and/or PAR-2 gene expression promoters. The additives may be any of the substances generally used in the art; the excipients, for example, may include such as lactin, sucrose, sodium chloride, glucose, starch, calcium carbonate, kaolin, microcrystalline cellulose and silicate; the binders may include such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, and polyvinyl pyrrolidone; the disintegrators may include such as dry starch, alginate sodium, agar powder, sodium bicarbonate, calcium carbonate, sodium lauryl sulfate, monoglyceride stearate and lactin; the lubricants may include such as purified talc, stearate, pyroborate, and polyethylene glycol; the flavoring agents may include such as sucrose, wild orange peel, citric acid and tartaric acid.

The liquid oral formulation of the subject compositions may conventionally be presented as an internal medicine, syrup, and elixir by optionally adding flavoring agents, buffers and stabilizers to the previously described PAR-2 activators and/or PAR-2 gene expression promoters. Flavoring agents may be any of the above described substances; buffers may be sodium citrate; and stabilizers may include such as tragacanth, acacia and gelatin.

The injectable solutions may conventionally be presented as subcutaneous, intramuscular and intravenous injections by optionally adding pH adjusters, buffers, stabilizers, tonicity agents and topical anesthetics to the previously described PAR-2 activators and/or PAR-2 gene expression promoters. pH adjusters and buffers may include such as sodium citrate, sodium acetate and sodium phosphate. Stabilizers may include such as sodium pyrosulfite, EDTA, thioglycolic acid and thiolactic acid. Topical anesthetics may include such as procaine hydrochloride and lidocaine hydrochloride. Tonicity agents may include such as sodium chloride and glucose.

Other dosage forms can be formulated by the same method known in the art. Pharmaceutical compositions for prevention and treatment of cerebral infarction thus provided according to the present invention are useful for preventing and treating the cerebral infarctions.

The preferable amount of preventive and therapeutic agents of the present invention as a PAR-2 activator and/or a PAR-2 gene expression promoter administered to the patients depends on the body weight, age and sex thereof, as well as condition of disease, formulation and a number of doses. The typical dose on an adult patient is a dose of 0.01 to 1000 mg, preferably a dose of 0.1 to 100 mg administered orally or parenterally, once or several times a day.

The present invention further provides a method of screening an active ingredient for preventing and treating cerebral infarction using as an indicator the PAR-2 activation promoted by a test substance. More precisely the invention provides a method to screen active ingredients for preventing and treating cerebral infarction, comprising the screening of the test substance with the function of activating PAR-2 or promoting expression of PAR-2 gene by contacting the test substances with a cell expressing PAR-2 to determine expression or activity of PAR-2.

The method of measuring PAR-2 activity according to the screening method of the present invention includes, but not limited to, the methods described in various literatures i.e. a series of cell assays such as measuring the change in the concentrations of $Ca^{2+}$ in a cell using cultured cell expressing PAR-2 such as the human umbilical vein endothelial cell or COS-1 cell wherein PAR-2 gene are introduced (J. Biol. Chem., 1997; 272:11133-11141) or measuring production of phosphorylated inositol (Proc. Natl. Acad. Sci. USA, 1997; 94:8884-8889); functional analyses such as a method for detecting endothelium-dependent vascular relaxation in the aorta of a rat (Can. J. Physiol. Pharmacol., 1995; 73:1203-7) or a method for detecting mucin secretion from the salivary gland of a rat (Biochemical and Biophysical Research Communications, 2000; 270:298-302).

EXAMPLES

The present invention is explained in more detail by the following examples, however, it should not be construed as limiting the invention in any manner.

Example 1

The present inventors performed following investigations using male PAR-2-deficient mice (homozygous deficient mice: PAR-2$^{-/-}$ mice) generated by backcrossing with CS7BL/6 mice for eight generation.

Initially, infarction volume in an infarction model was evaluated. More specifically, tMCAO model was prepared according to the methods of Connolly et al. (Neurosurgery, 1996; 38:523-531), wherein middle cerebral arteries (MCA) of a male PAR-2$^{-/-}$ mouse (KO) and a wild type mouse (WT) were blocked with a nylon suture under anesthesia, and after 60 minutes of the occlusion, blood flow was restored by withdrawal of the nylon suture. The brains were removed following decapitation at 24 hours after reperfusion, and 14 serial 10 μm-thick slices of longitudinal sections from each brain were cut at 600 μm intervals beginning at 1 mm from the front using a cryostat. Each slice was stained with cresyl violet, and the infraction area was measured with the use of computer-assisted image analysis software SigmaScan pro 5 (SPSS Inc.). Total infarct volume was calculated with the area of infarction and the distance between each slice, and values are expressed as mean±S.D.

The resulted representative cresyl violet stained image and infarction volume are shown in FIGS. 1A, 1B and 1C. Infarction area unstained by cresyl violet is significantly increased in KO (FIG. 1B) compared with WT (FIG. 1A), and infarction volume (FIG. 1C), was also significantly increased ($p<0.05$, Student's t-test) in KO ($38.9\pm14.4$ mm$^3$ (n=6)) compared with WT ($23.8\pm7.7$ mm$^3$ (n=6)). Thus, PAR-2 deficiency was revealed to be responsible for progression of cerebral infarction.

Example 2

Apoptosis assay was performed using KO and WT according to Example 1. The brains at 24 hours after tMCAO were examined to detect DNA fragmentation using terminal deoxynucleotidyl dUTP nick-end labeling (TUNEL) kit (Trevigen, Gaithers-burg, Md., USA). More specifically, the brains, at 24 hours after reperfusion, were removed following decapitation and quickly frozen in liquid nitrogen and cut on a cryostat to 10 μm thickness of longitudinal sections to include striatum. The frozen sections fixed by 4% paraformaldehyde were incubated with digoxigenin-labeled dUTP in the presence of terminal deoxynucleotidyl transferase (TdT) at 37° C. for 1 hour, followed by incubated with horseradish peroxidase-conjugated anti-digoxigenin antibody for 1 hour at room temperature. Then the sections were stained with diaminobenzidine, and the number of TUNEL positive cell stainings were counted in the three 1×1 mm$^2$ regions of the inner boundary zone of subsequent infarction to calculate mean±S.D.

The results were shown in FIGS. 2A, 2B and 2C. TUNEL positive cells are mainly distributed around the border in the area where the blood is supplied through MCA of WT and KO, and TUNEL staining is recognized basically in the cell nucleus (FIG. 2A (WT), FIG. 2B (KO)). Further, the number of positive cells in KO ($356.7\pm71.8$, n=6) was significantly increased ($p<0.05$, student's t-test) compared with WT ($261.2\pm41.3$, n=6) (FIG. 2C). Thus, PAR-2 deficiency in tMCAO model was revealed to be responsible for increase of apoptosis.

INDUSTRIAL APPLICABILITY

The present invention provides a method of prevention and treatment for cerebral infarction by activating PAR-2 and/or promoting the expression of PAR-2 gene. Particularly, the invention provides a method of preventing and treating cerebral infarction using a PAR-2 activator and/or a PAR-2 gene expression promoter. The present invention further provides a pharmaceutical composition for preventing and treating cerebral infarction comprising a PAR-2 activator and/or a PAR-2 gene expression promoter. The invention further provides a method of screening an active ingredient for preventing and treating cerebral infarction using as an indicator the PAR-2 activation promoted by a test substance. Accordingly, the present invention is extremely effective and has industrial applicability.

The invention claimed is:

1. A method of treating progression of cerebral infarction, comprising:
   administering an effective amount of at least one active ingredient selected from the group consisting of a PAR-2 activator and/or a PAR-2 gene expression promoter to a patient suffering from cerebral infarction.

2. The method according to claim 1, wherein the at least one active ingredient is selected from the group consisting of a PAR-2 ligand, trypsin, tryptase, tissue factor VIIa, tissue factor Xa, acrosin, and trypsin-like serine protease.

3. The method according to claim 2, wherein the PAR-2 ligand is a peptide having an amino acid sequence of SEQ ID NO. 1 or 2.

* * * * *